Figure 1:
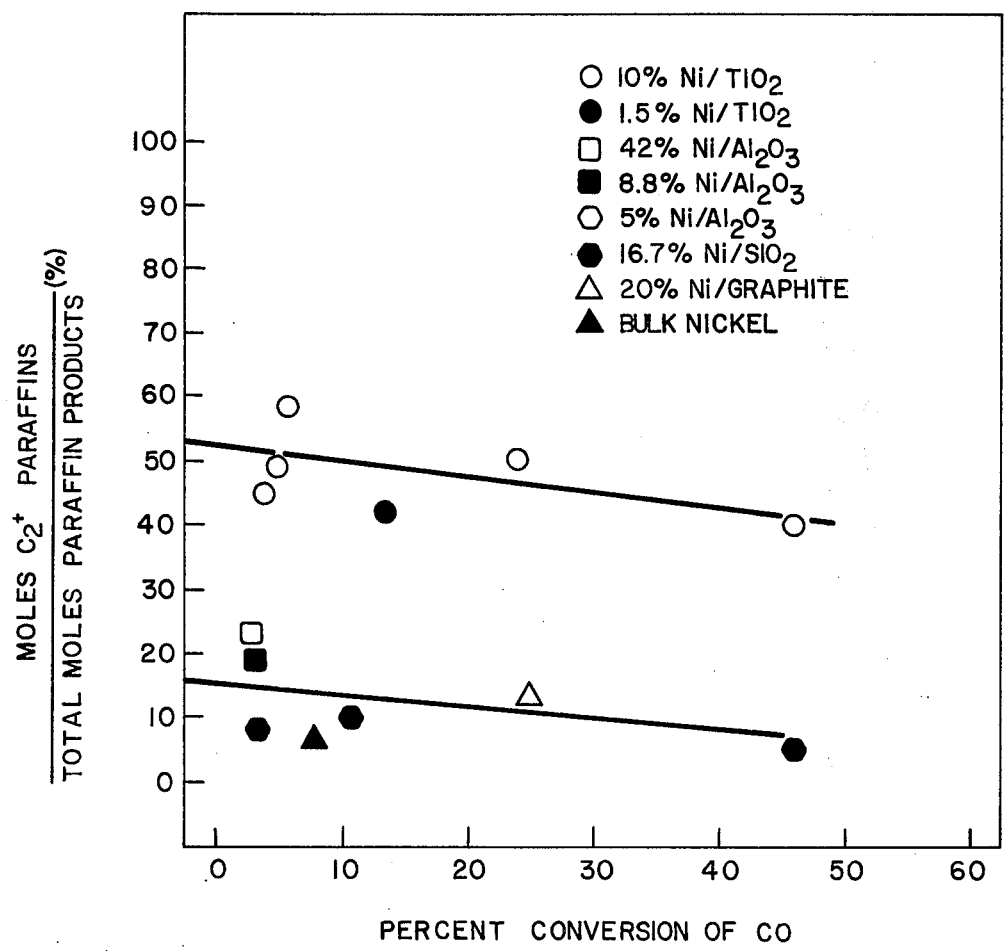

United States Patent [19]

Vannice et al.

[11] 4,042,615
[45] Aug. 16, 1977

[54] HYDROCARBON SYNTHESIS FROM CO AND $H_2$ USING Ni SUPPORTED ON A TITANIUM OXIDE

[75] Inventors: M. Albert Vannice, Plainfield; Robert L. Garten, Summit, both of N.J.

[73] Assignee: Exxon Research and Engineering Co., Linden, N.J.

[21] Appl. No.: 673,357

[22] Filed: Apr. 5, 1976

[51] Int. Cl.² .............................................. C07C 1/04
[52] U.S. Cl. ........................... 260/449.6 R; 252/459; 252/466 J
[58] Field of Search ................................... 260/449.6

[56] References Cited

U.S. PATENT DOCUMENTS

| | | | |
|---|---|---|---|
| 2,560,171 | 7/1951 | Hill | 260/449.6 |
| 2,637,739 | 5/1953 | McGrath | 260/449.6 |
| 2,850,515 | 9/1958 | Riblett et al. | 260/449.6 |

*Primary Examiner*—Howard T. Mars
*Attorney, Agent, or Firm*—Joseph J. Allocca; Ernest A. Forzano

[57] ABSTRACT

Nickel supported on $TiO_2$, other titanium-containing oxides or mixtures of various titanium oxides results in a catalyst system which exhibits superior hydrocarbon synthesis characteristics. Such supported nickel catalysts exhibit selectivity to paraffinic hydrocarbon products of from $C_2$ to $C_7$ which are free of olefins and oxygenated products. They generate CO conversions of up to 60% at pressures of 3090 kPa without significant change in product distribution. A large fraction of the product obtained contains 2 or more carbon atoms in the chain up to conversions of 60%. The supported nickel catalysts exhibit enhanced activity, improved selectivity to higher molecular weight normal paraffins, improved longevity and tolerance to sulfur and resistance to nickel carbonyl formation as compared to nickel catalysts on other supports such as $Al_2O_3$, silica or carbon.

A new method for the selective synthesis of higher molecular weight normal paraffins from CO and $H_2$ over a wide range of CO conversions at pressures of from 103 to 3090 kPa (1 atm = 103 kPa) which method comprises the steps of passing a synthesis gas stream of CO and $H_2$ at a ratio of from 2 moles CO per .2 to 20 moles $H_2$ at a space velocity of from 100 hr.$^{-1}$ to 30,000 hr.$^{-1}$ over a catalyst comprising from 0.01 to 75 wt. % nickel on $TiO_2$, other titanium-containing oxides or mixtures of said titanium-containing oxides for a time sufficient to effect the generation of desired paraffinic products, at a temperature of from 100 to 500° C. and a pressure of from 103 to $1.03 \times 10^5$ kPa. The supported nickel catalyst has a BET surface area of from 10 to 60 $m^2g^{-1}$ of total catalyst with a nickel crystallite size of < 10 nm (100 A).

21 Claims, 2 Drawing Figures

HYDROCARBON SYNTHESIS FROM CO AND $H_2$ USING NI SUPPORTED ON A TITANIUM OXIDE

This invention relates to a new and improved Fischer-Tropsch hydrocarbon synthesis process incorporating a catalyst of nickel on $TiO_2$, Ti-containing oxide support or mixed titanium oxides used therein. This catalyst has a number of desirable characteristics including increased activity, improved selectivity to higher molecular weight paraffins, life, sulfur tolerance, and resistance to nickel carbonyl formation.

Conventional state-of-the-art nickel catalysts, i.e. Ni/$Al_2O_3$, Ni/$SiO_2$ etc. are well known for their selectivity toward methane formation; for example see M. Greyson, "Catalysis", Vol. IV, 473 (1956) and H. A. Dirksen and H. R. Linden, Research Bulletin No. 31, Institute of Gas Technology (1963). Within a wide range of temperature, pressure and $H_2$/CO ratios methane is by far the predominant hydrocarbon product and it is this fact that has made nickel the catalyst of choice for commercial methane synthesis from CO and $H_2$.

Nickel has been dispersed on and co-precipitated with a wide variety of typical oxide supports and no major effect on product distribution has been noted. When higher hydrocarbons have been observed, they are still usually gaseous materials consisting primarily of ethane and only small quantities of $C_3^+$ hydrocarbons. The effect of a large number of promoters on the activity and selectivity of nickel catalysts has been studied and $ThO_2$ is the only material to have a pronounced influence on the product distribution. Usually used with Ni/Kieselguhr catalysts, the addition of 12-24 parts $ThO_2$ per 100 parts Ni results in up to 60-70 wt. % of the total hydrocarbon product present as $C_5^+$ material including solids and liquids (see R. B. Anderson, "Catalysis", Vol. IV, p. 53 (1956). No other promoters have been documented as being capable of inducing this change in product selectivity. Although catalyst activity was increased somewhat by the addition of $ThO_2$, the increases were not large, normally consisting of increases up to 10% in the $H_2$ + CO conversion.

Therefore, nickel catalysts have been used frequently in the past to synthesize methane from CO and $H_2$, and are quite selective in producing this product. With the exception of catalysts promoted with $ThO_2$, they were not known to possess the capability of producing large quantities of higher molecular weight products. This invention discloses the modification of the catalytic behavior of nickel by dispersing it upon $TiO_2$ or a Ti-containing support resulting in a catalyst which is employed in a process which yields a much higher average molecular weight product. The highly desirable effect of greatly increasing the activity of the nickel component is also obtained.

DESCRIPTION OF THE INVENTION

A new method for the selective synthesis of higher molecular weight normal paraffins from CO and $H_2$ over a wide range of CO conversions at pressures of from 103 to 3090 kPa which method comprises the steps of passing a synthesis gas stream comprising CO and $H_2$ at a $H_2$/CO ratio of from 0.1-10, preferably 0.5-4, most preferably 1-3 at a space velocity of from 100 hr.$^{-1}$ to 50,000 hr.$^{-1}$ over a catalyst comprising from 0.01 to 75 wt. % Ni on $TiO_2$, other titanium-containing oxides or mixtures of said titanium-containing oxides for a time sufficient to effect the generation of desired paraffinic products at a temperature of from 100° to 500° C., preferably 150°-400° C., most preferably 150°-300° C. and a pressure of from 103 - 1.03 $\times$ 10$^5$ kPa, preferably 103 - 3090 kPa, most preferably 103 - 2060 kPa. The supported nickel catalyst system used in the process has a total BET surface area of from 10 to 60 m$^2$g$^{-1}$ of total catalyst with a nickel crystallite size of less than 10 nm (100 A) (as measured by X-ray diffraction).

Nickel supported on $TiO_2$, other titanium-containing oxides or mixtures of titanium oxides results in a catalyst system which exhibits superior hydrocarbon synthesis characteristics. The titanium-containing oxide supports which are used in the practice of this invention are oxides having surface areas of from 1 to 200 m$^2$g$^{-1}$, preferably 10 - 100 m$^2$g$^{-1}$, most preferably 25 to 100 m$^2$g$^{-1}$. The oxides are selected from the group comprising $TiO_2$, $Al_2O_3$—$TiO_2$, $SiO_2$—$TiO_2$, $TiO_2$—Carbon, $ZrTiO_4$, alkaline earth titanates ($BaTiO_3$, $CaTiO_3$, $SiTiO_3$, $MgTiO_3$) alkali titanates ($Na_2TiO_3$, $K_2TiO_3$, $Li_2TiO_3$) and rare earth titanates, preferably the titanium oxide is $TiO_2$. With most supported metal catalysts the higher the surface area of the support the higher the dispersion of the supported metal at a given metal loading. It is therefore desirable to use a $TiO_2$ with as high a surface area as possible to maximize the dispersion of the metal. However, when working with $TiO_2$, samples with surface areas of 150 to 250 m$^2$g$^{-1}$ (usually prepared by precipitation techniques) desurface on heating to ~500° C. Commercially available $TiO_2$ made by flame hydrolysis of $TiCl_4$ has a stable surface area of ~60 m$^2$g$^{-1}$ for thermal treatments up to ~500° C. and is therefore the preferred support. Ni is deposited on the chosen support in a concentration of from 0.01 to 75 wt. %, preferably from 1.5 to 10 wt.%. Nickel is deposited on $TiO_2$ in a concentration from 0.01 to 75 wt.%, preferably from 1.5 to 10 wt.% and most preferably from 0.1 to 10 wt.%. The nickel deposited on the chosen support possesses a particle crystallite size as determined by standard techniques, such as X-ray diffraction or transmission electron microscopy, of from 1 to 30 nm, preferably 1 - 10 nm, most preferably 1 - 7.5 nm.

Using standard experimental techniques, 10% Ni/$TiO_2$ reduced in hydrogen at 450° C. (as in the following examples) evaluated by X-ray diffraction exhibited a crystallite size of ~7.5 nm which corresponds to a nickel dispersion of about 14%. For a 1.5% Ni/$TiO_2$ system, the particle size is less than 5 nm since Ni metal was not detectable by X-ray. This corresponds to a dispersion of greater than 20%.

Such supported nickel catalysts exhibit selectivity to paraffinic hydrocarbon products which are essentially free of olefins and oxygenated products. They can generate high CO conversions with a large fraction of the products obtained containing 2 or more carbon atoms in the chain. The supported nickel catalysts exhibit enhanced activity, improved selectivity to higher molecular weight normal paraffins, improved longevity and tolerance to sulfur and resistance to nickel carbonyl formation as compared to nickel catalysts of the prior art supported on materials such as $Al_2O_3$, $SiO_2$ or Carbon.

The nickel catalysts employed in the practice of the instant process are themselves prepared by techniques known in the art for the preparation of other catalyst systems such as Ni on $Al_2O_3$, etc. A suitable nickel salt, such as nickel nitrate, nickel acetate, etc. is dissolved in a solvent, such as water or any suitable solvent and stirred with the chosen titanium oxide system. Preferably, the support is $TiO_2$ prepared by flame hydrolysis of $TiCl_4$ which $TiO_2$ has a surface area of ~60 $m^2g^{-1}$. After thorough mixing the mixture is either allowed to dry and then heat treated in air at a temperature of from 100° to 150° C or alternatively may be dried in a single step by heating in air at a temperature of between 100° to 150° C. for several hours.

A supported $Bu/TiO_2$ catalyst can also be prepared by reduction of the compound $NiTiO_3$ which on reduction in hydrogen at temperatures of about 450° C. decomposes into nickel metal supported on $TiO_2$. Reduction of the stoichiometric $NiTiO_3$ to $Ni/TiO_2$ gives a catalyst of composition 38 wt. % $Ni/TiO_2$.

The final step, however, is the essential step of heat treating the supported nickel catalysts prepared as outlined above, or by similar techniques in a reducing atmosphere such as hydrogen at a temperature greater than 300° C., preferably greater than 400° C., most preferably greater than 500° C. for from 0.5 to 4 hrs, preferably 1-2 hrs.

The process described in the instant specification will selectively generate $C_2+$ normal paraffins from CO and $H_2$ in conjunction with the above outlined catalyst systems provided operation is conducted at a temperature below 500° C. Use of the above identified catalyst in the instant process also allows synthesis to be run at temperatures lower than those disclosed in the prior art with equivalent product yields and CO onversion rates and such superior results are obtained when using catalysts possessing Ni wt. loadings equal to those of the prior art.

EXAMPLE 1

Catalysts with improved activity and selectivity to normal paraffin products with carbon chain lengths of two and higher are obtained by depositing nickel on $TiO_2$ and other titanium-containing oxide supports. Thus, a 1.5% $Ni/TiO_2$ catalyst is prepared by stirring 11.4 ml of nickel nitrate solution containing 0.39 g of nickel with 25 g of $TiO_2$ in a beaker. The $TiO_2$ was prepared by flame hydrolysis of $TiCl_4$ and had a surface area of 60 $m^2g^{-1}$. Titania made by other techniques such as precipitation and calcination of a suitable titanium salt is also satisfactory. After thoroughly mixing the nickel solution with the $TiO_2$ the resulting material is dried in a dessicator overnight and further dried in air in an oven at 120° overnight. Alternatively the resulting material can be dried immediately at 120° C. in air for several hours. A 10% $Ni/TiO_2$ catalyst is prepared by mixing with a spatula in a beaker 20 g of $TiO_2$ with 11.1 g $NiNO_3.6 H_2O$ dissolved in 5 ml of distilled water. The resultant material is dried in a dessicator overnight and further dried at 120° C. in air overnight. By impregnating the dried 10% $Ni/TiO_2$ catalysts with additional quantities of nickel nitrate solution concentrations of $Ni/TiO_2$ up to ~75 wt. % can be obtained.

To illustrate the desirable characteristics of the Ni/$TiO_2$ catalysts, they were compared to several commercial nickel catalysts and to several supported nickel catalysts supported on $Al_2O_3$ and $SiO_2$. Thus a 5% Ni/$\eta$-$Al_2O_3$ catalyst was prepared by thoroughly mixing 9.5 g of $\eta$-$Al_2O_3$ having a surface area of 245 $m^2g^{-1}$ with 6.6 ml of nickel nitrate solution containing 0.5 g nickel. The resulting mixture wa dried overnight in air at 110° C. A 16.7% $Ni/SiO_2$ catalyst was prepared by thoroughly mixing 10 g of silica having a surface area of 300 $m^2g^{-1}$ with 20 ml of nickel nitrate solution containing 2 g of nickel. The resulting material was dried overnight in air at 110° C.

A series of supported nickel catalysts and bulk nickel oxide were reduced in hydrogen at 450° C for one hour prior to the introduction of a CO—$H_2$ feed at a temperature of 205° C. The enhanced activity of the $TiO_2$-supported nickel catalysts relative to a variety of other nickel catalysts is shown in Table I. The 10% $Ni/TiO_2$ catalyst is much more active on a per gram of catalyst basis than other nickel catalysts containing much larger quantities of nickel.

TABLE I

ACTIVITIES OF NICKEL CATALYSTS FOR CO-$H_2$ REACTION (CO-$H_2$ Reaction Conditions: 205° C, 103 kPa, $H_2$/CO=3)

| Catalyst[a] | μMoles CO Converted/Sec/ Gram Nickel | μMoles CO Converted/Sec/ Gram Catalyst |
|---|---|---|
| 5% Ni/$\eta$-$Al_2O_3$ | 3.44 | 0.172 |
| 8.8% Ni/$\eta$-$Al_2O_3$ | 1.63 | 0.143 |
| 42% Ni/$\alpha$-$Al_2O_3$ | 0.21 | 0.088 |
| 16.7% $Ni/SiO_2$ | 2.36 | 0.394 |
| 20% Ni/graphite | 0.064 | 0.082 |
| Bulk Ni Metal | 0.032 | 0.032 |
| 10% $Ni/TiO_2$ | 22.8 | 2.28 |
| 1.53% $Ni/TiO_2$ | 8.35 | 0.113 |

[a] All catalysts reduced 1 hr. at 450° C prior to activity test.

$TiO_2$ or titanium-containing oxide-supported nickel catalysts also exhibit desirable selectivity characteristics compared to bulk nickel or nickel on $SiO_2$ or $Al_2O_3$ supports. This is demonstrated in Table II. Nickel on a variety of supports, e.g. $Al_2O_3$, $SiO_2$, graphite, and bulk nickel produce methane almost exclusively with only small amounts of hydrocarbons with carbon chain lengths up to 4. The $TiO_2$ or titanium-containing oxide-supported nickel catalysts show a large reduction in methane make and increase in paraffin products with carbon chain lengths of two carbon atoms and higher. This is especially desirable for the production of storable liquid fuels from CO—$H_2$ mixtures obtained from coal gasification.

The increased selectivity of $TiO_2$ or titanium-containing oxide-supported nickel catalysts is maintained over a range of conversions up to ~50% as demonstrated in FIG. 1. Nickel catalysts prepared from other supports, however, show much poorer selectivity to high molecular weight paraffins than $TiO_2$ or titanium-containing oxide-supported metal catalysts.

The selectivity of the $TiO_2$ or titanium-containing oxide-supported nickel catalysts to hydrocarbons with carbon chain lengths of 2 and higher is also maintained at higher pressures compared to nickel on other supports. This is demonstrated in Table III. The behavior of the $Ni/TiO_2$ catalysts as a function of pressure for the production of higher molecular weight paraffins is opposite to that of $Ni/Al_2O_3$. As Table III shows it is most desirable to run the $Ni/TiO_2$ catalysts at low pressure to maximize production of higher molecular weight paraffins whereas high pressures are necessary for $Ni/Al_2O_3$. This is a desirable characteristic of $TiO_2$ or titanium-containing oxide-supported nickel catalysts since no compression of the synthesis gas would be required to operate a gasification-liquid fuels synthesis plant to maximize production of the desirable paraffin liquids.

EXAMPLE 2

The advantage of $TiO_2$ or titanium-containing oxide-supported nickel catalysts in suppressing the formation of nickel carbonyl in the presence of CO was demonstrated using infrared spectroscopy. Nickel is known to react with carbon monoxide to form volatile nickel carbonyl [$Ni(CO)_4$] which can result in a loss of nickel from the catalyst and the production of a poisonous effluent, i.e. $Ni(CO)_4$. The formation of $Ni(CO)_4$ is suppressed on $TiO_2$ or titanium-containing oxide-supported nickel catalysts compared to nickel on other supports such as $Al_2O_3$, $SiO_2$, and graphite.

TABLE II

SELECTIVITY OF NICKEL CATALYSTS

P = 103 kPa, $H_2/CO$ = 3

| Catalyst | T° C | % CO Conversion | Mole % Paraffin of each Carbon Number | | | | |
|---|---|---|---|---|---|---|---|
| | | | $C_1$ | $C_2$ | $C_3$ | $C_4$ | $C_5+$ |
| 10% Ni/$TiO_2$ | 243 | 24 | 50 | 9 | 25 | 8 | 9 |
| 1.5% Ni/$TiO_2$ | 251 | 13.3 | 58 | 14 | 12 | 8 | 7 |
| Bulk Ni | 252 | 7.9 | 94 | 6 | — | — | — |
| 42% Ni/$\alpha$-$Al_2O_3$ | 236 | 2.1 | 76 | 14 | 5 | 3 | 1 |
| 8.8% Ni/$\eta$-$Al_2O_3$ | 230 | 3.1 | 81 | 14 | 3 | 2 | — |
| 5% Ni/$\eta$-$Al_2O_3$ | 254 | 10.8 | 90 | 7 | 3 | 1 | — |
| 16.7% Ni/$SiO_2$ | 220 | 3.3 | 92 | 5 | 3 | 1 | — |
| 20% Ni/graphite | 234 | 24.8 | 87 | 7 | 4 | 1 | — |

TABLE III

SELECTIVITY OF NICKEL CATALYSTS AT VARIOUS PRESSURES (Reaction Conditions: $H_2/CO$ = 3, T = 200–206° C)

| Catalyst | Pressure (ATM) | % CO Conversion | Mole % Product | | | | |
|---|---|---|---|---|---|---|---|
| | | | $C_1$ | $C_2$ | $C_3$ | $C_4$ | $C_5^{30}$ |
| 10% Ni/$TiO_2$ | 1 | 4 | 50.5 | 21.5 | 7.5 | 7.5 | 12 |
| | 10 | 3.5 | 56 | 37 | 5.5 | 1.5 | — |
| | 20 | 4.5 | 57.5 | 35 | 5.5 | 2 | — |
| 31.4% Ni/$\alpha$-$Al_2O_3$ | 1 | 2.1 | 80 | 16 | 4 | 1 | — |
| | 10 | 1.9 | 69 | 29 | 2 | — | — |
| | 20 | 1.3 | 69 | 31 | — | — | — |

1 ATM = 103 kPa

The rate of $Ni(CO)_4$ formation from a 10% Ni/$TiO_2$ catalyst was compared to that from a 10% Ni/$SiO_2$ catalyst. The 10% Ni/$SiO_2$ catalyst was prepared by thoroughly mixing 10 g of $SiO_2$ having a surface area of 300 $m^2g^{-1}$ with 22 ml of nickel nitrate solution containing 1.11 g nickel. The resulting material was dried in air at 120° C overnight.

The 10% Ni/$TiO_2$ and 10% Ni/$SiO_2$ were, in separate experiments, pressed into thin wafers weighing 27–29 milligrams and charged to a cell identical to that described by D. J. C. Yates, W. F. Taylor and J. H. Sinfelt, J. Am. Chem. Soc., 86, 2996 (1964). The air was evacuated from the cell and hydrogen flow initiated through the cell at 12 l/hr. The cell was rotated so that the wafer was at the silica end of the cell which was then inserted into a furnace. The wafers were reduced in hydrogen for 1 hour at 500° C and evacuated for 10 min at the same temperature to remove hydrogen. The wafers were then cooled in vacuum to room temperature and the cell rotated so that the infrared windows were in the spectrometer beam. The wafers in these experiments were kept out of the infrared beam so that the formation of $Ni(CO)_4$ in the gas phase could be monitored by infrared spectroscopy.

Figure 2:
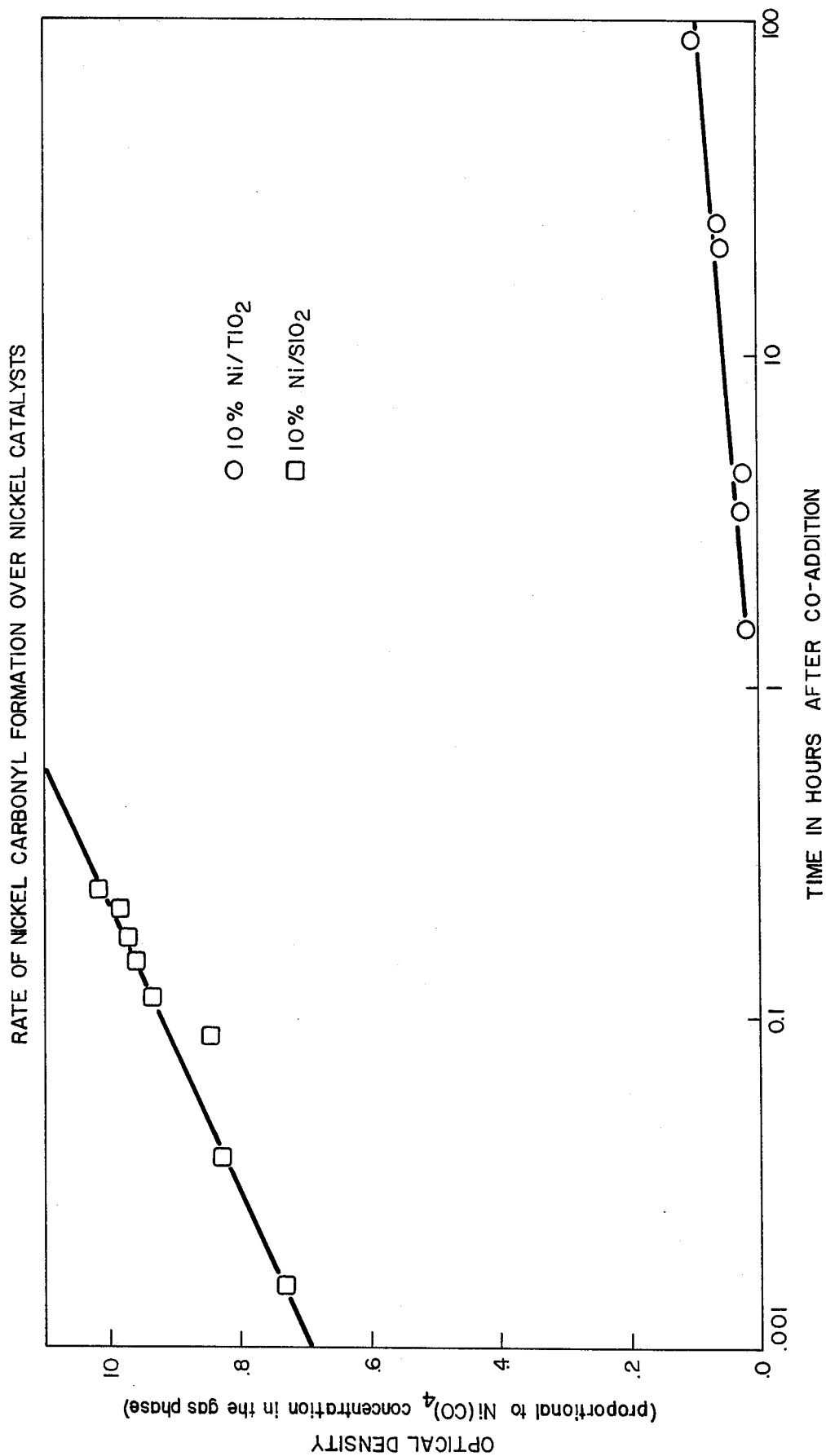

CO was added to each catalyst at a pressure of 1.87 kPa and the concentration of $Ni(CO)_4$ in the gas phase due to reaction of CO with nickel in the catalysts was followed as a function of time. FIG. 2 shows a plot of the optimal density of $Ni(CO)_4$ which is proportional to the concentration of $Ni(CO)_4$ in the gas phase around the catalyst as a function of time. The 10% Ni/$TiO_2$ catalyst is seen to be much less reactive toward $Ni(CO)_4$ formation than nickel on $SiO_2$. The $TiO_2$ and titanium-containing oxide-supported nickel catalysts thus have the desirable property of inhibiting the formation of $Ni(CO)_4$.

What is claimed is:

1. A process for the synthesis of higher molecular weight paraffins comprising the steps of passing CO and $H_2$ in a CO/$H_2$ ratio of 10 to 0.1 over a catalyst comprising nickel on a titanium-containing oxide support, wherein said titanium-containing oxide support is selected from the group consisting of $TiO_2$, $ZrTiO_4$, $TiO_2$-carbon, $TiO_2$—$Al_2O_3$, $TiO_2$—$SiO_2$, alkaline earth titanates, alkali titanates, rare earth titanates and mixtures thereof, at a space velocity of from 100 to 50,000 V/V/Hr. and a temperature of from 100° to 500° C and at pressures of from 103 to 1.03 × $10^5$ kPa for a time sufficient to effect the generation of the desired paraffinic products in the desired ratio, wherein the concentration of said nickel in said catalyst is from 0.01 to 75% by weight.

2. The process of claim 1 wherein the titanium-containing oxide is $TiO_2$.

3. The process of claim 2 wherein the $TiO_2$ has a surface area of from 25–100 $m^2g^{-1}$.

4. The process of claim 2 wherein the nickel-on-titanium oxide catalyst has a weight loading of nickel of from 0.1 to 10 wt. % based on total catalyst.

5. The process of claim 2 wherein the nickel-on-titanium oxide catalyst has a nickel crystallite size of from 1 to 10 nm (100 A).

6. The process of claim 2 wherein the CO/$H_2$ ratio is 4.0 to 0.5, the temperature is from 150° to 400° C and the pressure is from 103 to 3090 kPa.

7. The process of claim 2 wherein the CO/$H_2$ ratio is 3 to 1, the temperature is from 150° to 300° C and the pressure is from 103 to 2060 kPa.

8. The process of claim 2 wherein the nickel concentration is from 1.5 to 10% by weight.

9. The process of claim 2 wherein the catalyst consisting of nickel supported on $TiO_2$ has a nickel particle crystallite size of from 1 to 30 nm.

10. The process of claim 2 wherein the catalyst consisting of nickel supported on $TiO_2$ has a nickel particle crystallite size of from 1 to 7.5 nm.

11. The process of claim 2 wherein the $TiO_2$ has a surface area of from 1 to 200 $m^2g^{-1}$.

12. The process of claim 2 wherein the $TiO_2$ has a surface area of from 10 to 100 $m^2g^{-1}$.

13. The process of claim 1 wherein the titanium-containing oxide has a surface area of from 1 to 200 $m^2g^{-1}$.

14. The process of claim 1 wherein the nickel concentration is from 1.5 to 10 wt. %.

15. The process of claim 1 wherein the catalyst consisting of nickel supported on a titanium-containing oxide has a nickel particle crystallite size of from 1–30 nm.

16. The process of claim 1 wherein the catalyst consisting of nickel supported on a titanium-containing oxide has a nickel particle crystallite size of from 1 to 10 nm.

17. The process of claim 1 wherein the $CO/H_2$ ratio is 4.0 to 0.5, the temperature is from 150° to 400° C. and the pressure is from 103 to 3090 kPa.

18. The process of claim 1 wherein the $CO/H_2$ ratio is 3 to 1, the temperature is from 150° to 300° C. and the pressure is from 103 to 2060 kPa.

19. The process of claim 1 wherein the catalyst consisting of nickel supported on a titanium-containing oxide has a nickel particle crystallite size of from 1 to 7.5 nm.

20. The process of claim 1 wherein the titanium-containing oxide support has a surface area of from 10 to 100 $m^2g^{-1}$.

21. The process of claim 1 wherein the titanium-containing oxide support has a surface area of from 25 to 100 $m^2g^{-1}$.

* * * * *